(12) United States Patent
Singh et al.

(10) Patent No.: US 6,594,024 B1
(45) Date of Patent: Jul. 15, 2003

(54) MONITOR CMP PROCESS USING SCATTEROMETRY

(75) Inventors: Bhanwar Singh, Morgan Hill, CA (US); Ramkumar Subramanian, San Jose, CA (US); Khoi A. Phan, San Jose, CA (US); Bharath Rangarajan, Santa Clara, CA (US); Carmen Morales, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/886,863

(22) Filed: Jun. 21, 2001

(51) Int. Cl.[7] .................. G01B 11/28; B24B 49/00; B24B 51/00; G01N 21/86
(52) U.S. Cl. ............... 356/630; 451/6; 451/287; 451/41; 230/559.27
(58) Field of Search ............... 356/630; 451/6, 451/287, 41; 250/559.27

(56) References Cited

U.S. PATENT DOCUMENTS

| | | | |
|---|---|---|---|
| 5,413,941 A | * 5/1995 | Koos et al. ............... 438/16 |
| 5,795,495 A | 8/1998 | Meikle ............... 216/88 |
| 5,904,609 A | * 5/1999 | Fukuroda et al. ............... 451/285 |
| 5,964,643 A | * 10/1999 | Birang et al. ............... 451/285 |
| 6,292,265 B1 | * 9/2001 | Finarov et al. ............... 250/559.27 |
| 6,383,888 B1 | * 5/2002 | Stirton ............... 430/22 |
| 2002/0151987 A1 | * 10/2002 | Mendez ............... 700/8 |

* cited by examiner

Primary Examiner—John R. Lee
Assistant Examiner—Kalimah Fernandez
(74) Attorney, Agent, or Firm—Amin & Turocy, LLP

(57) ABSTRACT

One aspect of the present invention relates to an in-line system for monitoring and optimizing an on-going CMP process in order to determine a CMP process endpoint comprising a wafer, wherein the wafer is subjected to the CMP process; a CMP process monitoring system for generating a signature related to wafer dimensions for the wafer subjected to the CMP process; and a signature library to which the generated signature is compared to determine a state of the wafer. Another aspect relates to an in-line method for monitoring and optimizing an on-going CMP process involving providing a wafer, wherein the wafer is subjected to a CMP process; generating a signature associated with the wafer; comparing the generated signature to a signature library to determine a state of the wafer; and using a closed-loop feedback control system for modifying the on-going CMP process according to the determined state of the wafer.

26 Claims, 10 Drawing Sheets

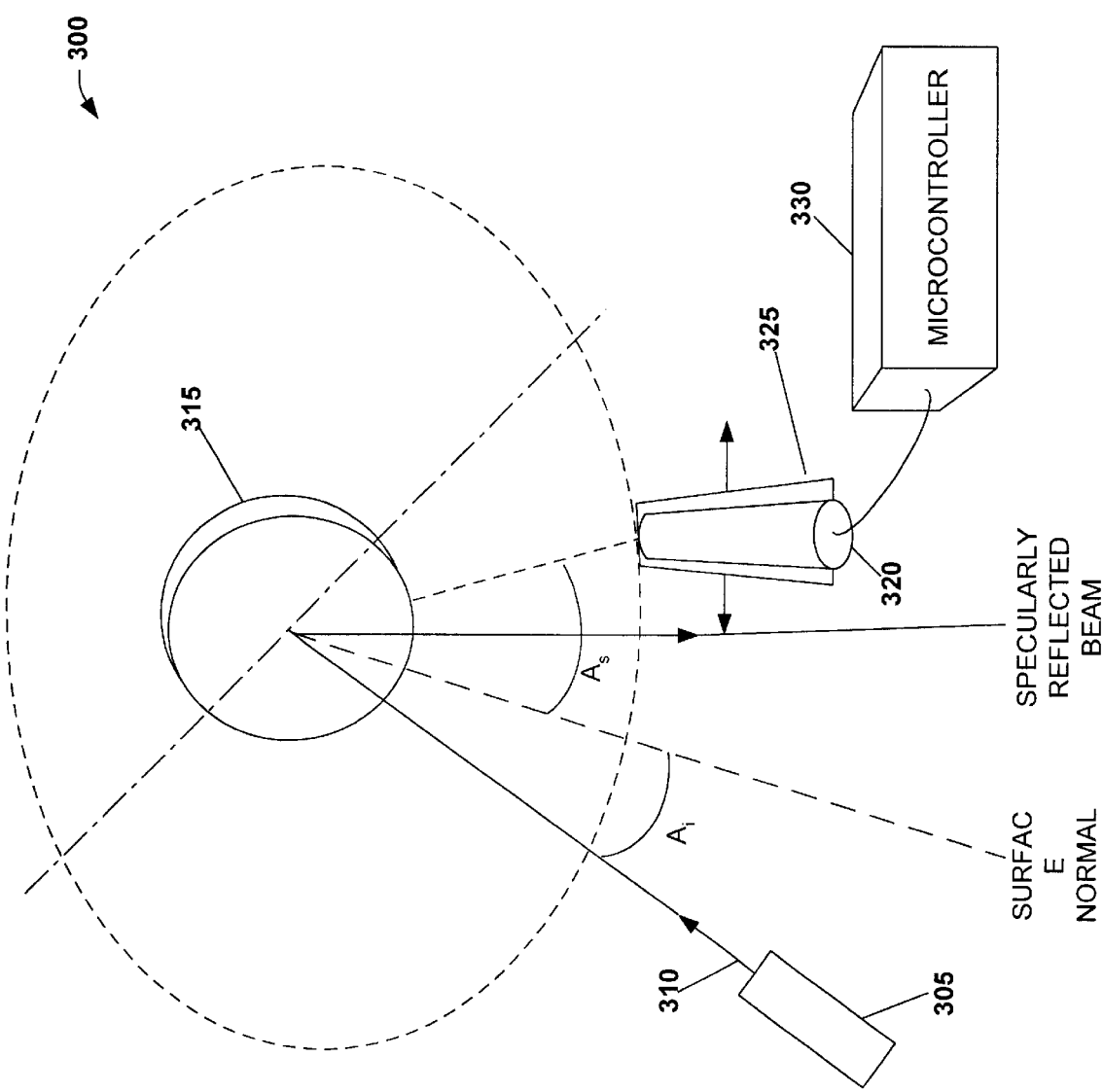

MONITOR CMP PROCESS USING SCATTEROMETRY

TECHNICAL FIELD

The present invention generally relates to processing a semiconductor substrate. In particular, the present invention relates to the in-line monitoring of an on-going CMP process using scatterometry to optimize and to determine an endpoint for the on-going CMP process.

BACKGROUND ART

In the semiconductor industry, there is a continuing trend toward higher device densities. To achieve these high densities, there has been and continues to be efforts toward scaling down device dimensions (e.g., at submicron levels) on semiconductor wafers. In order to accomplish such high device packing density, smaller and smaller feature sizes are required. This may include the width and spacing of interconnecting lines, spacing and size of memory cells, and surface geometry of various features such as corners and edges.

The requirement of small features with close spacing between adjacent features requires high resolution photolithographic processes. In general, lithography refers to processes for pattern transfer between various media. It is a technique used for integrated circuit fabrication in which a silicon slice, the wafer, is coated uniformly with a radiation-sensitive film, the photoresist, and an exposing source (such as optical light, x-rays, or an electron beam) illuminates selected areas of the surface through an intervening master template, the mask, for a particular pattern. The photoresist receives a projected image of the subject pattern. Once the image is projected, it is indelibly formed in the photoresist. The projected image may be either a negative or a positive image of the subject pattern. Exposure of the photoresist through a photomask causes the image area to become either more or less soluble (depending on the coating) in a particular solvent developer. The more soluble areas are removed in the developing process to leave the pattern image in the photoresist as less soluble polymer. are removed in the developing process to leave the pattern image in the photoresist as less soluble polymer.

The patterned photoresist is subsequently employed to replicate its pattern image onto one or more layers formed on the wafer. Layers of photoresist, conductive, polymeric and insulative materials are routinely applied to wafers multiple times during a manufacturing process for integrated circuits, as one of a sequence of steps to produce a desired lithographic pattern. Thickness and uniformity of the layers is critical to the overall functionality of the manufactured device. The goal of the photoresist application process as well as subsequent layering processes is to achieve uniform layers on the wafer surface. This goal can be achieved by planarizing the layers in order to obtain a desired thickness and uniformity.

One technique that is used in the semiconductor industry for planarizing layers is chemical mechanical polishing (CMP). Chemical mechanical polishing involves holding and rotating a semiconductor wafer against a wetted polishing platen under controlled chemical, pressure and temperature conditions. Typically a slurry solution is used as the abrasive fluid. The polishing mechanism is a combination of mechanical action and the chemical reaction of the material being polished with the slurry solution. As circuit densities increase, chemical mechanical polishing has become one of the most viable techniques for planarization. However, CMP is not without its share of difficulties.

Conventional CMP processes check planarization parameters near or at the end of polishing or at pre-scheduled intervals of time. These types of post-polishing and interval detection methods can be problematic for several reasons. For example, pre-scheduled interval endpoint detection methods are generally based on past wafer characteristics. Thus, they may not account for structural and layer variations which may exist among wafers. As a result, over, under, or uneven polishing may occur despite the interval endpoint detection method employed. Although some poorly polished wafers may be reparable, repair costs and associated manufacture delays may be too burdensome and less cost-effective than discarding them. Furthermore, poor polishing may cause irreparable damage, forcing the damaged wafers to be discarded.

In addition, post-CMP detection methods do not provide a user with real-time information relating to the polishing (smoothing) of the wafer, thereby making it difficult to determine when to terminate a given CMP process before an appropriate endpoint has passed. Furthermore, post-CMP data limits the user to large-scale estimations for determining an appropriate CMP endpoint, resulting in recurring polishing errors, which contribute to yield loss, increased manufacturing costs and decreased performance in the semiconductor devices. In light of these problems, there is an unmet need for monitoring the CMP process in order to determine an appropriate endpoint for terminating the polishing process. In addition, there is an unmet need for optimizing an on-going CMP process.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention provides an in-line system and an in-line method for monitoring a CMP process with respect to a layer or wafer undergoing planarization and/or smoothing. More specifically, the present invention provides an in-line system and an in-line method for determining a termination point for an on-going CMP process and for optimizing the on-going CMP process to affect current and future wafers. This is accomplished in part by conducting the CMP process with scatterometry feedback corresponding to a thickness and a profile of the wafer.

One aspect of the present invention relates to an in-line system for monitoring a CMP process containing a wafer, wherein the wafer is subjected to the CMP process; a CMP device comprising one or more CMP components, wherein the CMP device performs the CMP process; a CMP process monitoring system for generating a signature associated with wafer dimensions undergoing a CMP process step; a signature library to which the generated signature is compared to determine a state of the wafer; and a closed-loop feedback control system for modifying the on-going CMP process according to the determined state of the wafer structure.

Another aspect of the present invention relates to an in-line system for measuring thickness and profile of a wafer undergoing a CMP process containing a CMP device comprising one or more CMP components, wherein the CMP device performs the CMP process; a light source for directing light at a wafer, wherein the wafer is subjected to the CMP process; a light detector for collecting the light reflected from the wafer; a signature library comprising signatures associated with known wafers which have been subjected to the CMP process; a CMP analysis system, operatively coupled to the light detector and the signature library for generating a signature corresponding to the reflected light to determine dimensions of the wafer undergoing the CMP process; and a closed-loop feedback control system for optimizing the CMP process according to the determined wafer dimensions to make one or more changes to the CMP device.

Yet another aspect of the present invention relates to using scatterometry in an in-line system for determining an endpoint of a CMP process. The system contains a CMP device comprising one or more CMP components, wherein the CMP device performs the CMP process; a light source for directing light at a wafer, wherein the wafer is subjected to the CMP process; a light detector for collecting the light reflected from the wafer; a signature library comprising signatures associated with known wafers which have been subjected to the CMP process; a CMP analysis system, operatively coupled to the light detector and the signature library for generating a signature associated with the reflected light to determine dimensions of the wafer undergoing the CMP process; a CMP controller operatively coupled to the CMP monitoring system and a CMP driving system for determining the endpoint of the CMP process, wherein the CMP controller operatively controls the CMP process via the CMP driving system using closed-loop feedback control; and a trained neural network operatively connected to the CMP controller to facilitate optimization of the CMP process.

Still yet another aspect of the present invention relates to an in-line method for monitoring a CMP process by generating a signature corresponding to a wafer undergoing a CMP process. The method involves the steps of providing a wafer, wherein the wafer is subjected to a CMP process; generating a signature associated with the wafer; comparing the generated signature to a signature library to determine a state of the wafer; and using a closed-loop feedback control system for modifying the on-going CMP process according to the determined state of the wafer structure.

Still another aspect of the present invention relates to using scatterometry in an in-line, closed-loop method for determining an endpoint to a CMP process. The method involves the steps of providing a wafer, wherein the wafer is subjected to a CMP process; directing a beam of incident light at the wafer; collecting light reflected from the wafer; generating a signature associated with the wafer; comparing the generated signature to a signature library to determine dimensions of the wafer; determining whether the wafer dimensions are within a pre-determined acceptable range; if the wafer structure dimensions are within the acceptable range of values, then instructing a CMP driving system via a controller to terminate the CMP process; and if the wafer structure dimensions are not within the acceptable range of values, then instructing the CMP driving system via a controller to adjust one or more CMP process components and to continue the CM P process for the wafer structure.

BRIEF DESCRIPTION OF DRAWINGS

FIG. 10 illustrates a schematic diagram of an exemplary scatterometry system according to one aspect of the present invention.

DISCLOSURE OF INVENTION

Figure 1:
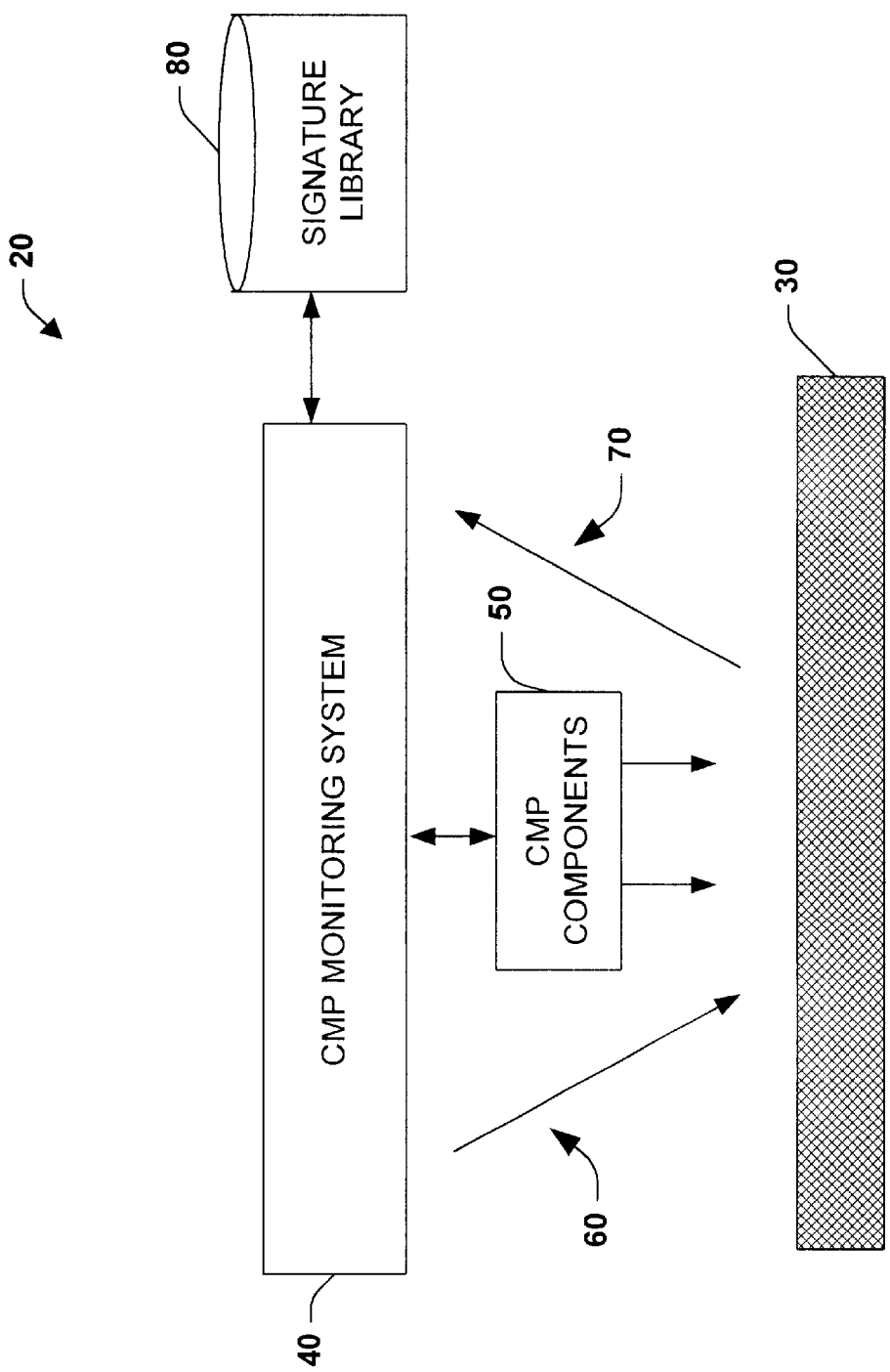
FIG. 1 illustrates a high-level schematic diagram of a system according to one aspect of the present invention.

The present invention involves an in-line system and an in-line method for monitoring a chemical mechanical polishing (CMP) process and determining an appropriate termination point or endpoint for an on-going CMP process. One aspect of the present invention more specifically relates to an in-line system and an in-line method employing scatterometry feedback to measure dimensions (e.g., a thickness and a profile) of a layer or wafer as it proceeds through the on-going CMP process. As a result of the present invention, the determination of an endpoint in and optimization of the on-going CMP process are facilitated. Since a CMP endpoint for a particular wafer and/or layer can be determined, improved performance and product reliability is obtainable which leads to reduced wafer yield loss.

In the present invention, a wafer structure, which may include a layer thereon, (hereinafter, referred to as "subject wafer") is about to be or is subjected to a conventional CMP process. The conventional CMP process may be performed by a conventional CMP device involving one or more CMP process components. Generally, as the CMP process progresses, the polishing process and the subject wafer are monitored in order to determine a suitable endpoint for the CMP process. In particular, dimensions of the subject wafer are monitored as the wafer continues through the CMP process. Examples of wafer dimensions include a thickness and a profile of the wafer structure, wafer surface, and layer of the subject wafer. Examples of layers that can be polished or planarized include metal layers, insulation layers such as oxides, nitrides and low-k materials, polysilicon layers and amorphous silicon layers.

Monitoring the subject wafer as it proceeds through the polishing process effectively allows one to visualize the wafer's appearance and progress in order to effectively optimize the on-going polishing process. As the subject wafer approaches a desired thickness and/or desired profile, the endpoint of the CMP process can be determined, thereby mitigating ineffective polishing as well as wafer yield loss.

The CMP process may be monitored and optimized in part by a scatterometry system. The concept and principles of scatterometry are described in greater detail below. See FIG. 10. According to one aspect of the present invention, scatterometric data is generated by directing light at the subject wafer and by collecting light reflected from the subject wafer. The reflected light corresponds to a current state of the subject wafer. That is, the light reflected from the wafer directly relates to the thickness and/or profile of the subject wafer. A light detecting device collects the reflected light and/or light data and transmits this information to a CMP monitoring system.

The CMP monitoring system monitors the CMP process by analyzing light data received from the light detectors in accordance with scatterometry techniques and principles. The light data may be transformed or translated into scatterometric data. Scatterometric data typically consists of a signature generated from analysis of the reflected light with respect to the incident light. Therefore, the generated signature corresponds to a current state of the subject wafer at a particular time during the CMP process. The generated signature may be compared to a database or signature library composed of any number of known signatures related to wafers which have undergone similar CMP processes. When a match is found, the state (i.e., dimensions) of the subject wafer can be determined by the CMP monitoring system and fed back into the polishing process/system in order to optimize polishing for the current and future wafers. Wafer dimensions include, for example, the thickness and/or profile of the subject wafer as well as other dimensions relating to, affected by, or involved in the polishing process. Due to the non-invasive, non-destructive nature of scatterometry, scatterometric data may be gathered at frequent intervals which facilitates sequence analysis of the CMP process.

The scatterometric data may also be used by a controller. The controller is operatively coupled to the CMP monitoring system. According to one aspect of the present invention, the controller receives information in connection with the subject wafer and/or related data from the CMP monitoring system. The controller uses this information to control a CMP device which includes one or more CMP process components via a CMP driving system. Specifically, the CMP driving system can serve to translate and implement the controller's instructional commands as well as to process information received from the controller in order to implement such commands. Alternatively, the CMP driving system may transmit instructional commands and/or information received from the controller directly to the one or more CMP process components. Examples of the one or more CMP process components may include at least one of a device, tool, composition, meter or system or a combination thereof which are employed to carry out a conventional CMP process.

The present invention facilitates controlled feedback of information in order to effect one or more changes in an on-going CMP process. For example, according to one aspect of the invention, information fed back to the CMP driving system may signal the CMP driving system to either continue the polishing process or to terminate the polishing process. Termination may occur either immediately or at a determined time. According to another aspect of the invention, the CMP driving system may be signaled to adjust one or more CMP process components according to a determined state of the subject wafer. Such adjustments or modifications to the CMP process components may be necessary in order to achieve the determined endpoint. A trained neural network or similar device, as later described in FIGS. 3–4 and 9, may be incorporated to facilitate making such optimal modifications to the CMP process. For example, the trained neural network may be incorporated into a system for monitoring a CMP process and programmed to correlate and/or evaluate CMP process parameters, measurements, and other data generated and determined in the course of carrying out the present invention.

It should be appreciated that various aspects of the present invention may employ technologies associated with facilitating unconstrained optimization and/or minimization of error costs associated with the CMP process. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed in the present invention.

Referring initially to FIG. 1, a high-level schematic illustration of a system 20 for monitoring a CMP process is shown. The system 20 includes a wafer 30, wherein the wafer 30 is going to be or is being subjected to a CMP process. The system 20 also includes a CMP process monitoring system 40 operatively coupled to a CMP device (not shown). The CMP device performs the polishing process and includes one or more CMP process components 50.

The CMP monitoring system 40 may be a stand-alone device and/or may also be distributed between two or more cooperating devices and/or processes. The CMP monitoring system 40 may reside in one physical or logical device such as a computer or process and/or be distributed between two or more physical and/or logical devices. The CMP monitoring system 40 may include one or more components that are located inside a process chamber and/or one or more components that are not located inside a process chamber. The CMP process components 50 may be employed in planarization, smoothing, and/or roughening processes depending on the desired application.

The CMP monitoring system 40 is operatively coupled to one or more CMP process components 50. The one or more CMP process components 50 work cooperatively with the CMP monitoring system 40. By way of illustration, the one or more CMP process components 50 receive and implement instructional commands from the CMP monitoring system 40. The CMP monitoring system 40 formulates the instructional commands by generating and analyzing data relating to, for example, one or more dimensions of the wafer 30.

The CMP monitoring system 40 generates this data by directing a beam of incident light 60 at the wafer 30 and collecting a light 70 which is reflected and/or refracted from the wafer 30. The incident light 60 may be supplied by many different light sources, for example, a frequency stabilized laser. The CMP monitoring system 40 may direct the light 60 at substantially all of the wafer 30 or at pre-selected regions of the wafer 30. For example, the CMP monitoring system 40 may direct the incident light 60 at selected regions of the subject wafer 30 such that these regions provide data sufficient to generate scatterometry signatures. The reflected light 70 is collected by the CMP monitoring system 40 and analyzed using scatterometry techniques in order to generate a signature. The generated signature facilitates determining one or more wafer dimensions and/or one or more CMP process parameters 90 associated with the subject wafer 30.

Wafer dimensions include but are not limited to a thickness and a profile of the subject wafer 30. CMP process parameters 90 (not shown) include but are not limited to slurry or liquid solution type 91, pH of polishing solution 92, solution flow rate 93, polishing time 94, applied pressure of polishing device/tool 95, length of planarization 96 and polishing speed 97 (collectively referred to as CMP process parameters 90). It should be appreciated that use of a slurry in the CMP process is optional and not required by all CMP processes. Therefore, the slurry is not required to carry out the present invention.

The CMP process monitoring system 40 includes a scatterometry system for analyzing scatterometric data generated by collecting the reflected light 70. Scatterometry analysis may include comparing one or more generated signatures with one or more known signatures contained in a signature library 80. Such signatures may be generated by combining reflected light 70 measurements to produce a signature associated with that reflected light 70 pattern.

As the CMP process progresses, signatures associated with the wafer 30 (or layer undergoing CMP process) may be generated continuously or at frequent intervals throughout the CMP process. For example, light reflected from wafer 30 at time T1 produces a signature S1 which corresponds to a wafer thickness H1 and/or a wafer profile P1. Similarly, light reflected from the wafer 30 at time T3 produces a signature S3 which corresponds to a wafer thickness H3 and/or a profile P3. Analyzing the sequence of signatures can facilitate determining whether the wafer 30, or layer, is being polished uniformly and/or whether the wafer 30 is being polished, for example, at the desired speed, length of time, pressure and/or planarization length.

Feedback information can be generated from such sequence analysis to maintain, increase or decrease one or more of the CMP process components in order to modify an on-going polishing process. For example, information related to the sequence analysis can be fed back to the CMP process components 50 where the one or more components 50 may be modified or optimized to effect one or more changes in the on-going CMP process. Such modifications may include altering the polishing rate and/or pressure in order to determine and/or achieve an appropriate endpoint for the CMP process.

The CMP process monitoring system is operatively coupled to the signature library 80. The signature library 80 may store data in various forms such as, but not limited to, one or more lists, arrays, tables, databases, linked lists and data cubes. The signature library 80 may be located on one or more physical devices such as, for example, disk drives, tape drives, and/or memory units.

Analyses, including sequence analyses, associated with the reflected light 70 and/or known signatures stored in the signature library 80 may be employed to control the one or more CMP process components 50. It should be understood that the CMP process components 50 may be employed to polish, smoothen and/or roughen a wafer surface in an even or uneven manner depending on the desired application. Because the CMP process may be employed at intermediate layers as well as at the top layer of a wafer structure, determining the appropriate endpoint for the CMP process is critical to the overall performance of the wafer/device.

Figure 2:
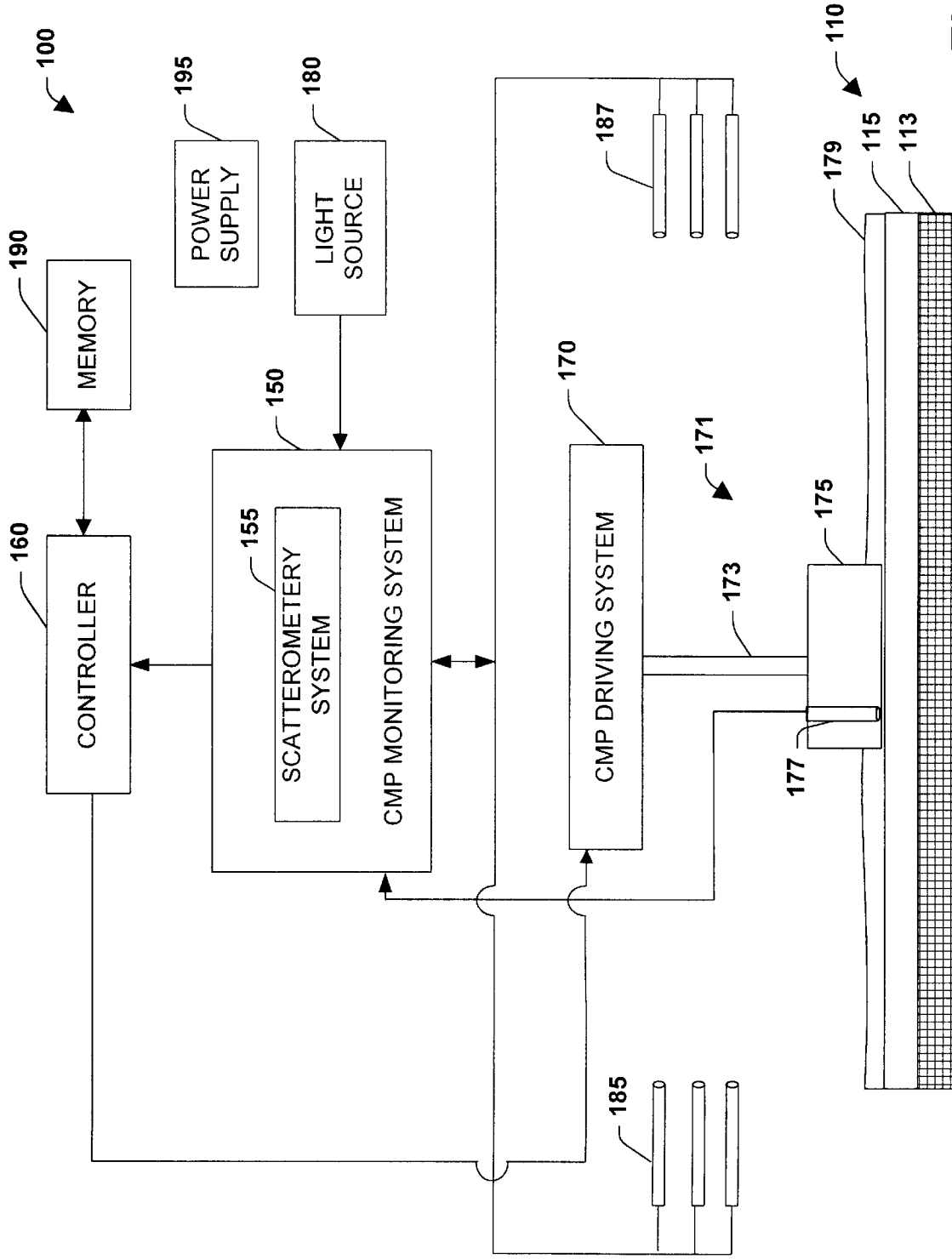
FIG. 2 illustrates a schematic block diagram of a system according to one aspect of the present invention.

Turning now to FIG. 2, a system 100 for monitoring a CMP process and determining an endpoint using scatterometry is shown. According to one aspect of the invention, the system 100 possesses controlled-feedback capabilities to implement one or more changes in the CMP process for future wafers. According to another aspect, the system 100 is a closed-loop system with controlled feedback capabilities to facilitate optimization of the CMP process for a wafer currently being polished and for future wafers.

The system 100 includes a wafer 110 (layer 115 and substrate 113) which is about to undergo or is undergoing a CMP process. The system 100 also includes a CMP monitoring system 150, a controller 160 and a CMP driving system 170 which operate cooperatively in order to control a CMP device 171 and to facilitate determining an endpoint in the CMP process. In particular, the CMP monitoring system 150 is operatively coupled to the controller 160 which regulates the CMP driving system 170. The CMP driving system 170 selectively controls the CMP device 171. The CMP device 171 performs the polishing process and includes one or more CMP process components such as, for example, a spindle 173, a polishing pad 175, an optical wave guide 177 (optical fiber), and/or a polishing liquid 179.

The CMP driving system 170 receives information and/or instructional commands from the controller 160 based upon its analysis of data transmitted from and collected by the CMP monitoring system 150. The controller 160 may include a processor (not shown) for determining the content and type of information to be transmitted to the CMP driving system 170. For example, the CMP monitoring system 150 gathers the reflected light data and performs an analysis of that data using scatterometric techniques or methods. The analyzed data is then transmitted to the controller 160. The controller 160 processes the analyzed data by determining the content and type of information to be transmitted to the CMP driving system 170. Thus, the controller 160 and/or the driving system 170 may selectively regulate or control the CMP device 171 connected to or associated with the CMP driving system 170.

Moreover, the cooperative interaction between the monitoring system 150, the controller 160 and the driving system 170 facilitates optimizing the CMP process as it progresses. To that end, polishing errors may be mitigated and increased efficiency in semiconductor fabrication achieved.

Still referring to FIG. 2, the components associated with the system 100 are now described in greater detail. The CMP monitoring system 150 is operatively connected to one or more target light sources 185 and one or more light detectors 187. The target light source 185 projects light onto the wafer 110, which is about to be or is being subjected to the CMP process. The light may be one or more beams of light such as a laser; however, other types of light suitable to carry out the present invention may be employed. The light may be projected onto the entire surface of the wafer 110 or at selected regions of the wafer 110 surface. The light reflected from the wafer 110 is collected by the one or more light detectors 187. It should be appreciated that the light may also refract from the wafer 110 surface.

The CMP monitoring system 150 analyzes the collected light data using a scatterometry system 155 and generates a signature. Analysis of the collected light involves determining at least one dimension related to the subject wafer 110 according to scatterometric principles. For example, a thickness and/or a profile of the wafer 110 and/or layer 115 can be measured and compared to a desired thickness and/or desired profile. The reflected light is measured with respect to the incident light in order to obtain the various dimensions relating to either the subject layer 115 or wafer 110 or both.

It should be appreciated that any suitable scatterometry system 155 may be employed to carry out the present invention. Furthermore, such systems are contemplated to fall within the scope of the claimed invention.

The system 100 also includes a light source 180 which supplies light to the target light sources 185 through or via the CMP monitoring system 150. The light source 180 may be a frequency-stabilized laser; however it should be understood that any laser or other light source suitable for carrying out the present invention may be employed. Other examples include a laser diode or a helium neon gas laser.

The collected light data may also be further analyzed by the controller 160. The controller 160 is operatively coupled to the CMP driving system 170. Therefore, the CMP driving system 170 is at least in part regulated by the controller 160. The CMP driving system 170 selectively controls the CMP device 171, as well as the one or more CMP process components, at least in part according to the information received from the controller 160. The controller 160 can determine the progress of the CMP process as well as the most current state of the subject wafer 110 and/or layer 115.

According to one aspect of the present invention, the controller 160 can process the measured thickness $H_m$ to determine an appropriate endpoint for the current CMP process. For example, the measured thickness may be compared to stored signatures. Each stored signature may include a set of CMP process parameters which if implemented, facilitates determining a termination or endpoint. When a match is found, the set of CMP process parameters may be analyzed by the controller 160 and implemented by the CMP driving system 170 to achieve an appropriate endpoint for the current CMP process. The controller 160 may transmit all or part of the set of CMP process parameters to the CMP driving system 170 depending on the current CMP process parameters. Hence, the controller 160 selectively regulates the one or more CMP process components via the CMP driving system 170 in order to determine a termination point of the on-going CMP process.

As described above, the controller 160 may include a processor (not shown). Such processor, or central processing unit, may be any of a plurality of processors, such as the AMD K7, the AMD Athlon™, the AMD Duron™, and other similar and/or compatible processing units. The controller 160/processor may be programmed to control and operate the various components within the system 100 in order to carry out the various functions described herein.

The controller 160 may also be operatively coupled to a memory 190. The memory 190 serves to store information such as, for example, program code executed by the controller 160 for carrying out operating functions of the system 100 as described herein. By way of illustration, the memory 190 can hold patterns or signatures or other data to which observed (measured) data can be compared. The memory 190 also serves as a storage medium for temporarily storing CMP process parameters and measured wafer and/or layer dimensions such as CMP process progress values, CMP process progress tables, component coordinate tables, wafer and/or layer shapes and sizes, scatterometry information, achieved wafer and/or layer dimensions, desired wafer and/or layer dimensions as well as other data that may be employed to facilitate the performance of the present invention.

The system 100 is powered by a power supply 195. Such power supply 195 may be any suitable power supply, such as a battery and/or line power, necessary to carry out the present invention.

Figure 3:
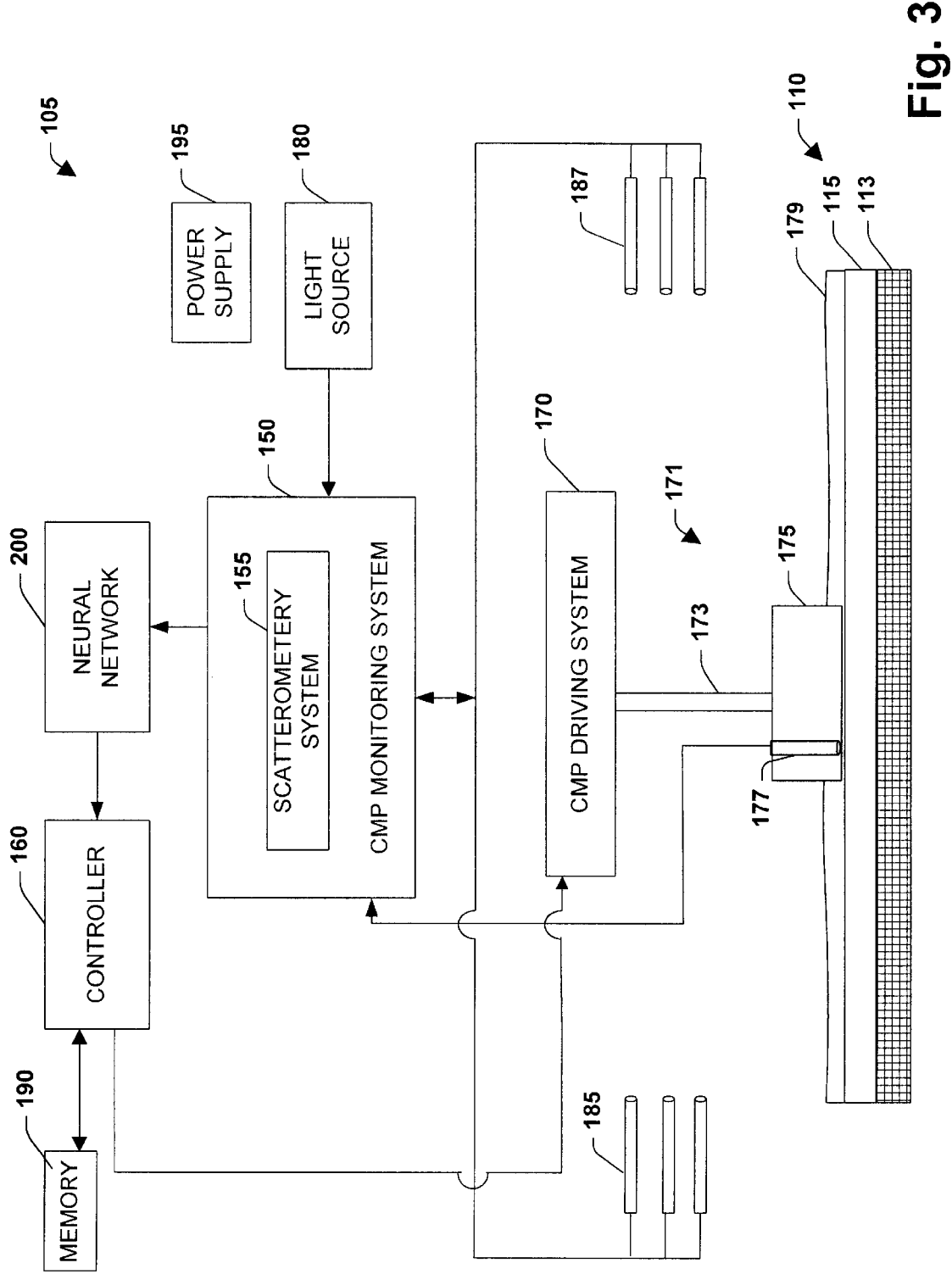
FIG. 3 illustrates a schematic block diagram of a system including a neural network according to one aspect of the present invention.

Referring now to FIG. 3, a CMP monitoring, optimization and endpoint determination system 105 is shown which is similar to the system 100. The CMP monitoring and endpoint determination system 100 described in FIG. 2 may also include a trained neural network (TNN) 200 for detecting and diagnosing problems within the one or more CMP process parameters 90 associated with the collected light data and generated signature. The TNN 200 can determine the necessary adjustments to be made to the one or more CMP process parameters 90 by evaluating the parameters 90 as they existed at the time the light data was detected and collected. Operation of the TNN 200 is illustrated in FIG. 4.

Figure 4:
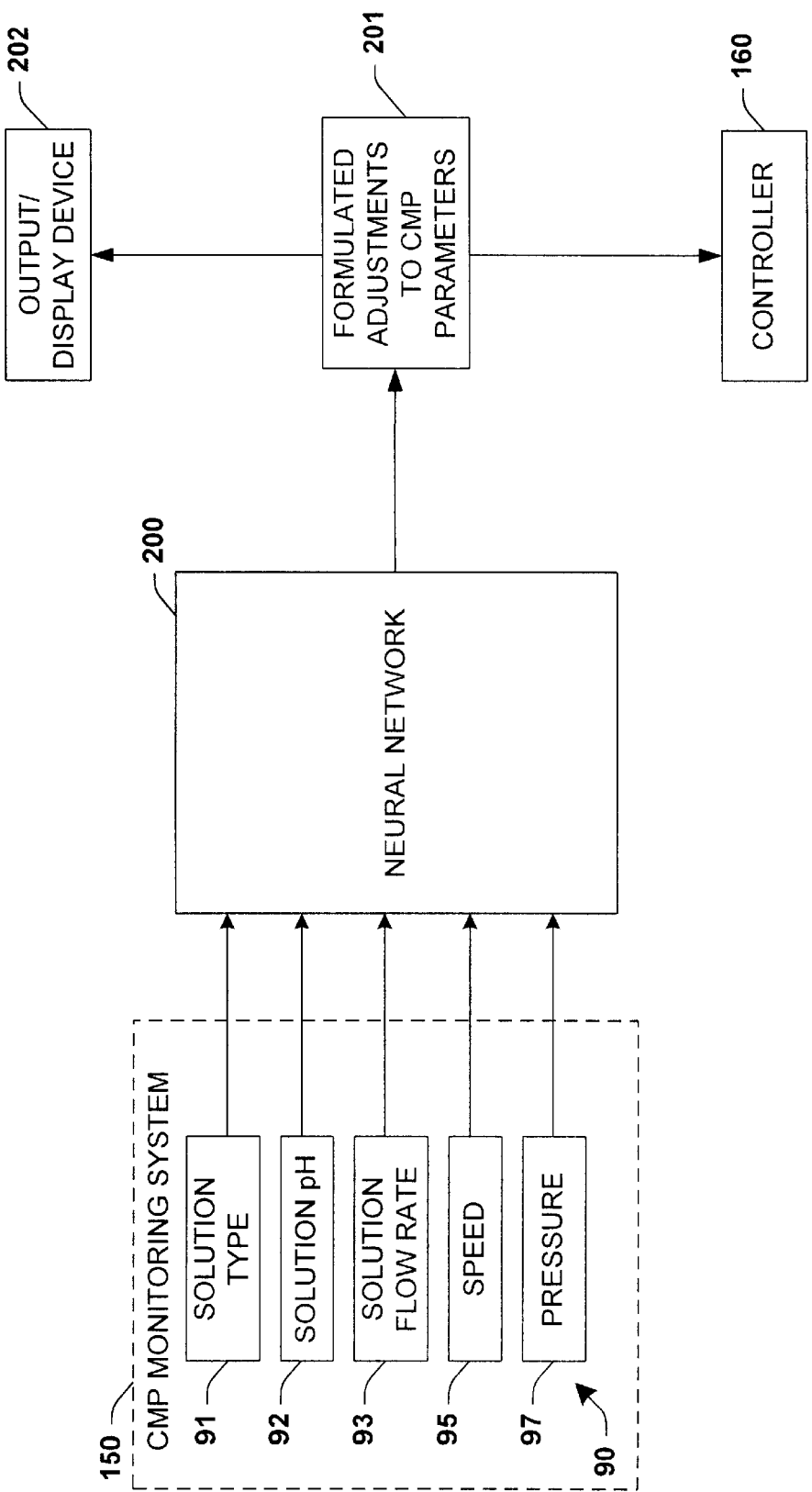
FIG. 4 illustrates a high-level schematic diagram of a neural network employed in the system of FIG. 3 according to one aspect of the present invention.

As can be seen in FIG. 4, the TNN 200 may receive input data from the CMP monitoring system 150 such as, for example, CMP process parameters 90 and/or the corresponding generated signature. Examples of CMP process parameters include slurry or polishing solution type 91, solution pH 92, solution flow rate 93, polishing speed 95 and applied pressure 97. The TNN 200 processes the parameter and/or signature information or data and outputs a listing 201 including one or more adjustments to make to the one or more CMP process parameters 90. The listing 201 may then be transmitted to the controller 160 for implementation. The controller 160 may translate the listing information into informational commands and then may transmit those commands to the CMP driving system 170, as described in FIG. 2. Alternatively or in addition, the listing 201 may then be transmitted to an output/display device 202 for operator evaluation.

The TNN 200 may also function to detect parameter-adjustment implementation errors (not shown in FIG. 4). That is, the TNN 200 may be programmed to remember past listings 201 of adjustments made to the one or more CMP process parameters 90. Therefore, if the TNN 200 receives input data (e.g., CMP process parameters 90) that does not reflect an adjustment which was previously commanded, then the TNN 200 outputs an error signal corresponding to the particular parameter. For example, at time $T_5$, the TNN 200 receives input data relating to generated signature $S_5$ and the corresponding process parameters 91, 92, 93, 95 and 97. According to the generated signature $S_5$ and the process parameters, TNN 200 determines that the solution pH 92 and the solution flow rate 93 require downward adjustments which are specific to each parameter. Information relating to these adjustments are transmitted to the controller 160 and then to the CMP driving system 170 for effective implementation. However, at time $T_6$, the input data associated with the solution flow rate 93 indicates that the previous adjustment was not properly implemented (i.e., solution flow rate 93 increased indicating an upward adjustment).

The generated error signal indicates the solution flow rate and alerts the system 105 and/or an operator via the output/display device 202 of the error and its source (e.g., solution flow rate). The TNN 200 may also be programmed to indicate the extent to which one or more CMP process parameters 90 have deviated from the prescribed adjustment (s). For example, the solution flow rate at time $T_6$ increased 1.5 times from its reading at time $T_5$. Thus, the TNN 200 has the capabilities to facilitate optimization of the CMP process by prescribing CMP process parameter adjustments and further by detecting internal adjustment implementation errors.

FIGS. 5–8 are described in detail below with respect to the CMP monitoring and endpoint determination system 100. However, it should be understood that the present invention contemplates that the system 105 may also be employed.

Figure 5:
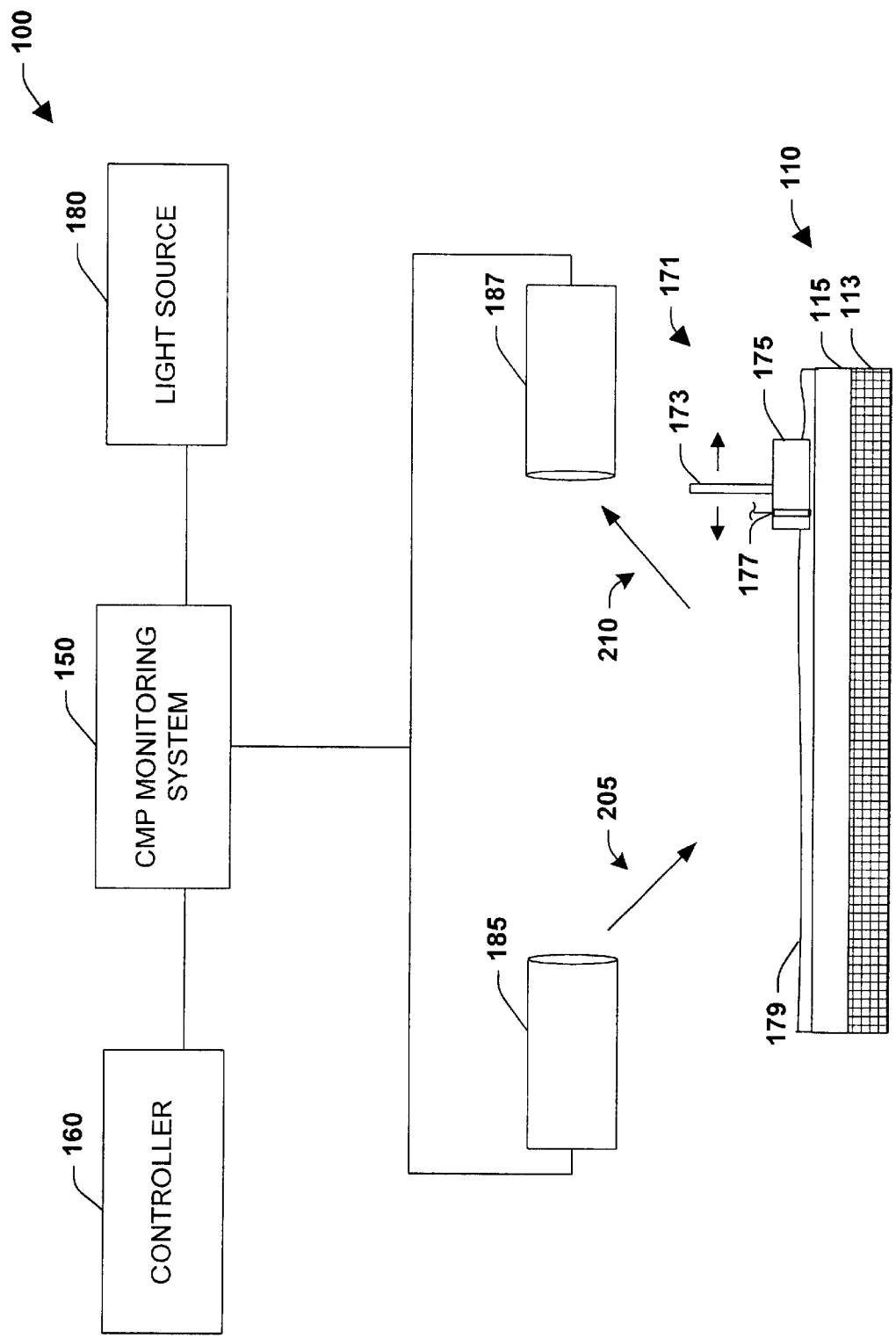
FIG. 5 illustrates a schematic, partial block diagram of a system employed in a CMP process according to one aspect of the present invention.

Turning now to FIG. 5, one aspect of the system 100 in use is shown. FIG. 5 illustrates the system 100 being employed to monitor a chemical mechanical polishing process in order to determine a CMP endpoint. As shown, the wafer 110 (top layer 115 and substrate 113) is undergoing a CMP process; however, it should be appreciated that the system 100 may operate on any wafer structure which is about to undergo such a process. On the surface of the wafer 110, the polishing liquid 179 is applied in a manner and in amount depending on the desired application. The CMP device 171 components such as, for example, the spindle 173, the polishing pad 175 and the optical wave guide 177 are positioned to begin the polishing process. Before and/or during the polishing process, the CMP monitoring system 150 may be employed. The target light source 185 projects one or more beams of light 205 onto the layer 115 (top surface of wafer 110). Reflected light 210 is detected by the one or more light detectors 187 and collected by the CMP monitoring system 150 according to scatterometry techniques.

The CMP monitoring system 150 analyzes the collected light and/or related data and generates a signature using scatterometry techniques. Analysis of the collected light and/or related data may involve comparing the collected light data to stored light data to determine a state of the layer 115 (at the time the light was projected 205 and reflected 210 from the layer 115). Determining the state of the layer 115 includes determining layer dimensions such as a thickness and a profile of the layer 115 for either the whole length of the layer 115 or selected portions of the layer 115. The generated signature and/or related data are transmitted to the controller 160 where it is processed into information and instructional commands in a form usable to the CMP driving system (FIG. 2). Processing performed by the controller 160 may also involve comparing the measured CMP processing parameters to known CMP processing parameters in order to determine a proper endpoint for the current CMP process.

The CMP monitoring system 150 provides to the controller 160 direct, real-time measurements and observations related to the current state of the layer 115 and/or wafer 110 as the CMP process progresses. Providing real-time, direct measurements to the controller 160 and to the CMP driving system (FIG. 2) facilitates a more precise determination of a CMP process endpoint over conventional CMP endpoint detection systems and methods.

Figure 6:
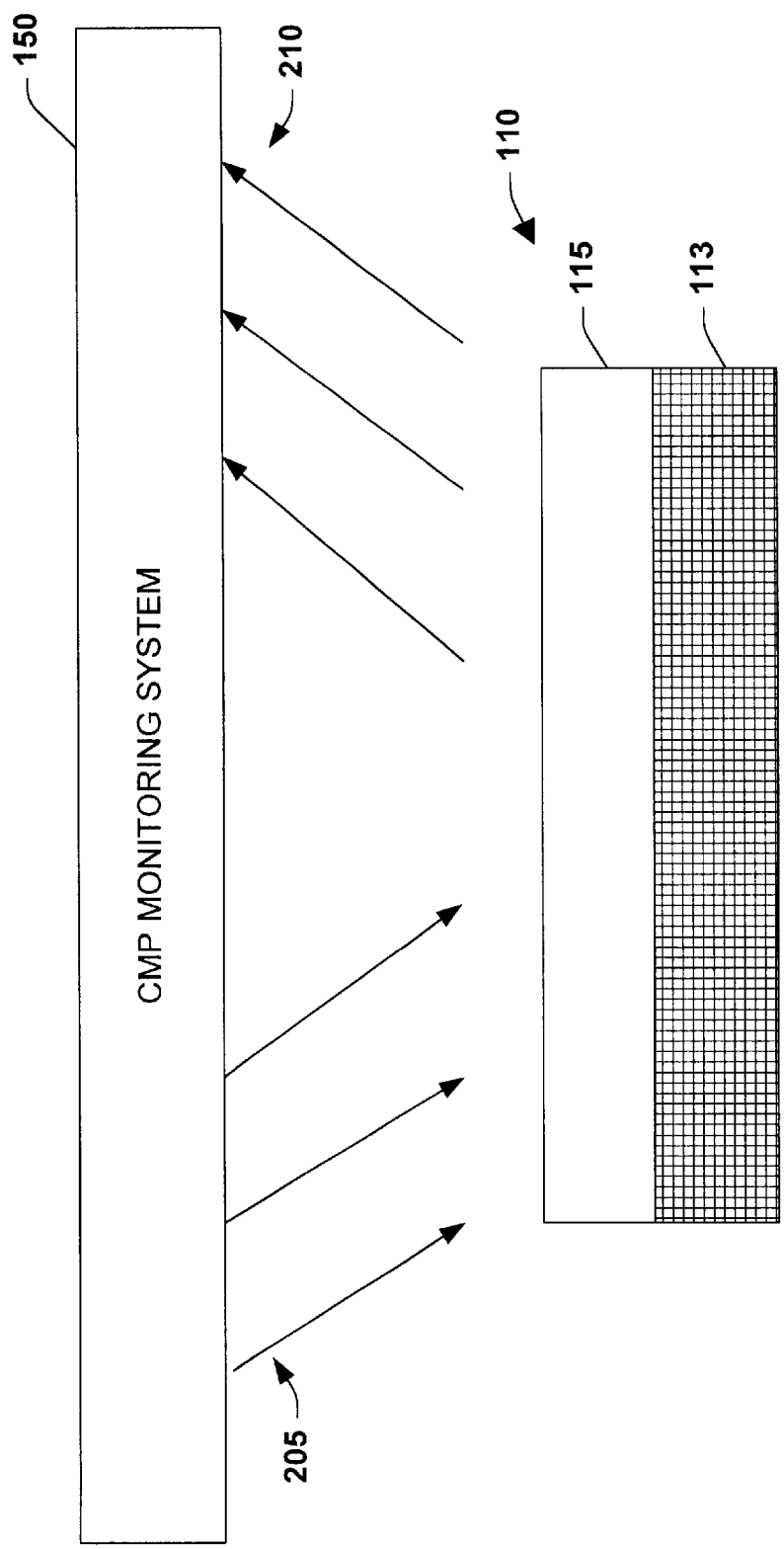
FIG. 6 illustrates a cross-sectional diagram of a wafer undergoing a CMP process according to one aspect of the present invention.
Figure 7:
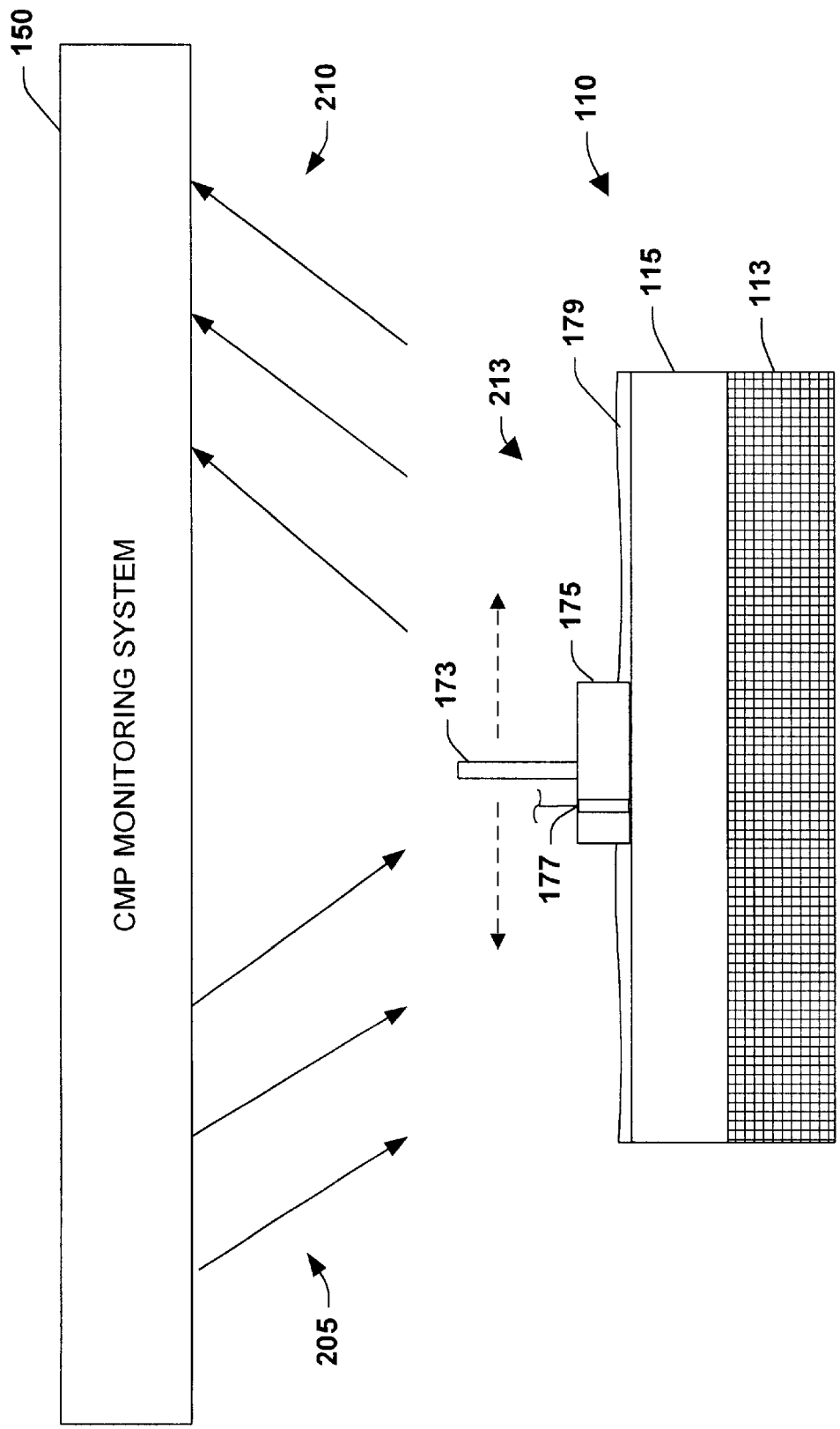
FIG. 7 illustrates a cross-sectional diagram of a wafer undergoing a CMP process according to one aspect of the present invention.
Figure 8:
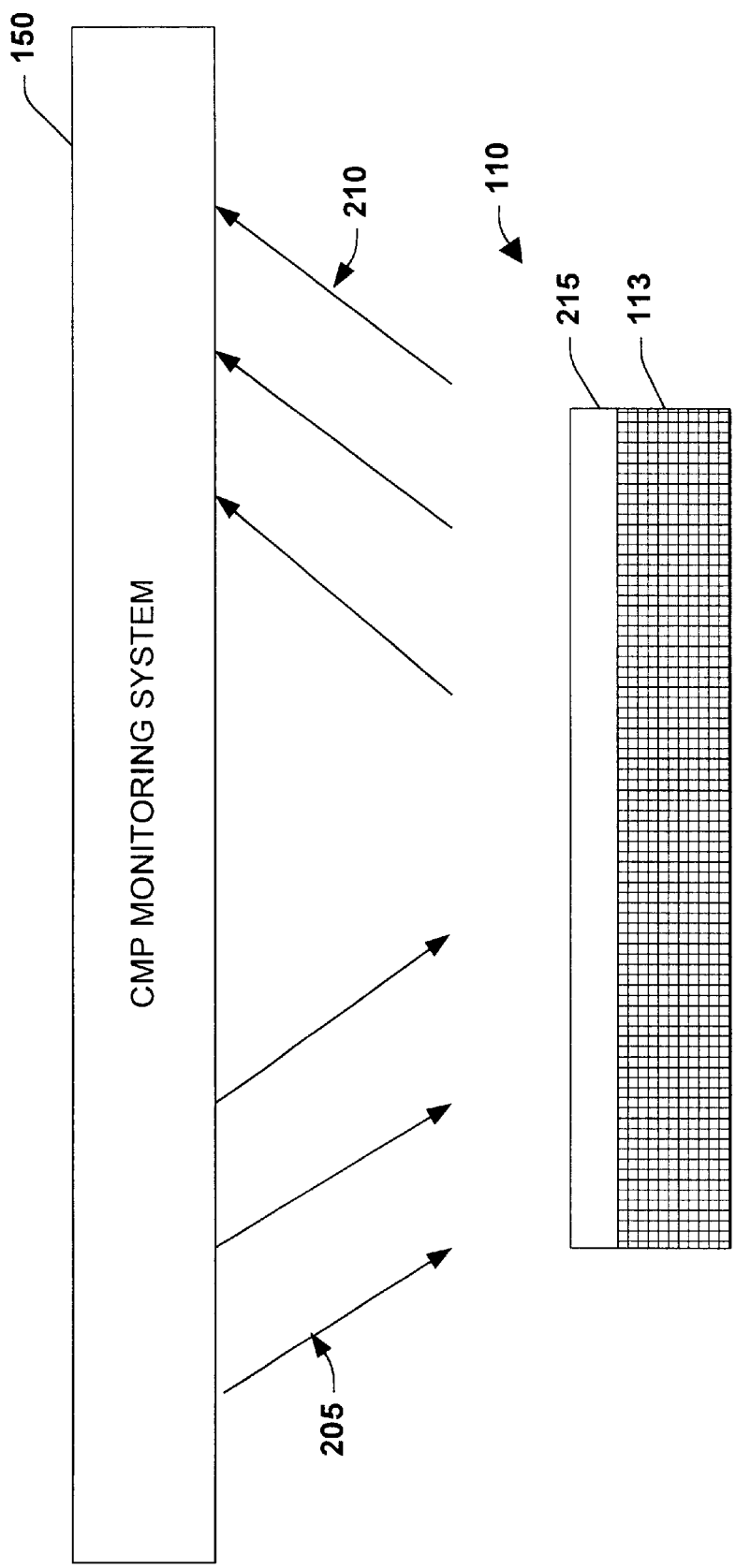
FIG. 8 illustrates a cross-sectional diagram of a wafer undergoing a CMP process according to one aspect of the present invention.

FIGS. 6–8 illustrate the CMP process monitoring system 150 being employed in a conventional CMP process from the time before the process begins ($T_0$) to the time the process ends ($T_E$). In FIG. 6, the incident light 205 is directed at the wafer 110 (i.e., layer 115). The entire length and/or selected portions of the wafer 110 may be monitored and measured in order to determine the progress of the CMP process and a CMP process endpoint. The incident light 205 may be projected onto the wafer 110 at simultaneous, multiple beams of light 205 at a fixed angle in order to obtain these measurements. The monitoring system 150 then collects the light 210 which reflects off of the wafer 110 (layer 115). It should be appreciated that one or more beams of incident light 205 may be employed and one or more beams of reflected light may be collected to carry out the present invention.

Measurements taken at $T_0$ may be used to ascertain the initial state (e.g., thickness and profile) of the wafer 110 just prior to polishing. Measurements corresponding to the initial dimensions of the wafer 110 may also be used to determine the extent or degree of polishing that has occurred at some later time ($T_n$) during the CMP process. Furthermore, comparing the state of the layer at $T_0$ and $T_n$ may facilitate determining an endpoint for the CMP process.

In FIG. 7, the CMP monitoring system 150 is being employed to monitor the wafer 110, and in particular layer 115, while a CMP process 213 is in progress. The spindle 173, polishing pad 175 and optical wave guide 177 process components move (indicated by dashed arrows) across the layer 115 over which the polishing liquid 179 has been applied. As the CMP process components 173, 175 and 177 move across the layer 115, the CMP monitoring system 150 continually projects the light 205, collects the reflected light 210 and analyzes the collected light data in order to determine an endpoint of the CMP process 213. In particular, as the process 213 progresses, the CMP monitoring system 150 is able to gather real-time information relating to the layer being polished and controllably feed that information back to the CMP driving system (and CMP process components) via the controller 160 (FIG. 2). Thus, the CMP monitoring system 150 facilitates determining a CMP process endpoint with increased precision and control.

FIG. 8 shows the wafer 110 following completion of the CMP process 213 (FIG. 7). As can be seen, the wafer 110 now has a polished layer 215. The CMP monitoring system 150 may continue to operate as described above at the completion of the CMP process 213 to verify the accuracy of the system-determined endpoint.

Figure 9:
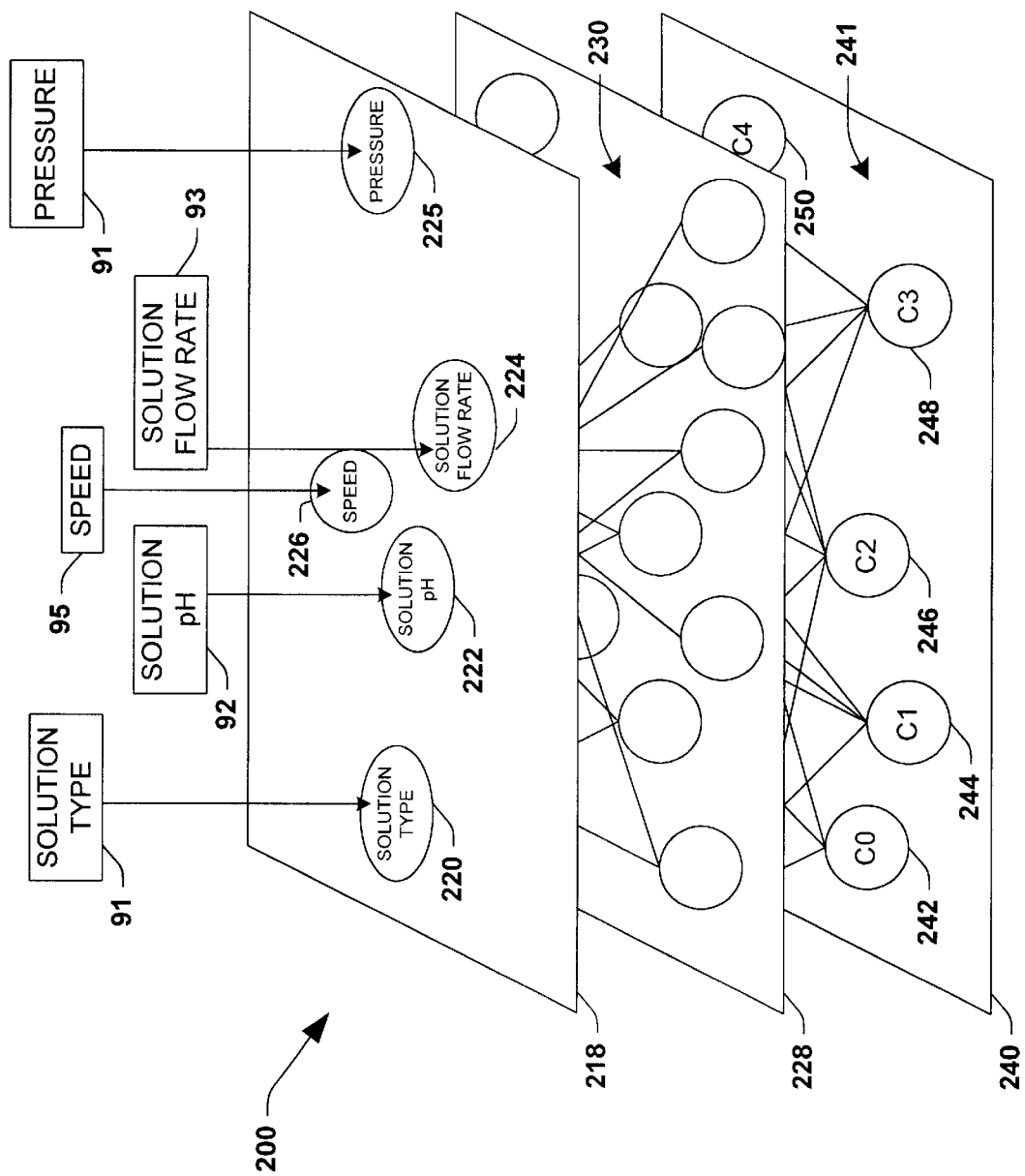
FIG. 9 illustrates a schematic diagram of an explemplary neural network according to one aspect of the present invention.

Referring now to FIG. 9, the exemplary neural network 200 comprises an input layer 218 having neurons 220, 222, 224, 225, and 226 corresponding to the solution type, solution pH, solution flow rate, applied pressure to the polishing tool, and polishing speed, respectively, received from sensors or detecting devices (not shown) of the CMP monitoring system 150. One or more intermediate or hidden layers 228 are provided in the network 200, wherein any number of hidden layer neurons 230 may be provided therein. The neural network 200 further comprises an output layer 240 having a plurality of output neurons corresponding to pre-determined polishing/process parameter classification values of the class 241. Thus, for example, the output layer 240 may comprise output neurons 242, 244, 246, 248, and 250 corresponding to class values 0, 1, 2, 3, and 4, respectively, whereby the neural network 200 may output an adjustment listing 201 indicative of necessary adjustments to the one or more CMP process parameters 90 as well as to the existence and extent of adjustment implementation errors in the monitoring system (e.g., system 105) with which it is associated.

In this regard, the number, type, and configuration of the neurons in the hidden layer(s) 228 may be determined according to design principles known in the art for establishing neural networks. For instance, the number of neurons in the input and output layers 218 and 240, respectively, may be selected according to the number of attributes (e.g., pressures, flow, speed, etc.) associated with the system 105, and the number of parameter classes 241. In addition, the number of layers, the number of component neurons thereof, the types of connections among neurons for different layers as well as among neurons within a layer, the manner in which neurons in the network 200 receive inputs and produce outputs, as well as the connection strengths between neurons may be determined according to a given application (e.g., CMP monitoring system) or according to other design considerations.

Accordingly, the invention contemplates neural networks having many hierarchical structures including those illustrated with respect to the exemplary network 200 of FIG. 9, as well as others not illustrated, such as resonance structures. In addition, the inter-layer connections of the network 200 may comprise fully connected, partially connected, feed-forward, bi-directional, recurrent, and off-center or off surround interconnections. The exemplary neural network 200, moreover, may be trained according to a variety of techniques, including but not limited to back propagation, unsupervised learning, and reinforcement learning, wherein the learning may be performed on-line and/or off-line. For instance, where transitions between classes are continuous and differences between classes of process parameters are slight, it may be difficult to use unsupervised learning for the purpose of adjustment-implementation error detection, in which case supervised learning may be preferred, which may advantageously employ back propagation. In this regard, training of the classifier may be done on a sufficient amount of training data covering many CMP process parameter degrees (e.g., severities) and operating conditions of the monitoring system. Furthermore, the training of the network 200 may be accomplished according to any appropriate training laws or rules, including but not limited to Hebb's Rule, Hopfield Law, Delta Rule, Kohonen's Learning Law, and/or the like, in accordance with the present invention.

FIG. 10 illustrates an exemplary scatterometry system 300 collecting reflected light. Light from a laser 305 is brought to focus in any suitable well-known manner to form a beam 310. A sample, such as a wafer 315, is placed in the path of the beam 310 and a photo detector or photo multiplier 320 of any suitable well-known construction. Different detector methods may be employed to determine the scattered power. To obtain a grating pitch, the photo detector or photo multiplier 320 may be mounted on a rotation stage 325 of any suitable well-known design. A micro-controller 330, of any suitable well-known design, may be used to process detector readouts, including, but not limited to, angular locations of different diffracted orders leading to diffraction grating pitches being calculated. Thus, light reflected from the sample 315 may be accurately measured.

Scatterometry is a technique for extracting information about a surface upon which an incident light has been directed. Scatterometry is a metrology that relates the geometry of a sample to its scattering effects. Scatterometry is based on the reconstruction of the grating profile from its optical diffraction responses. Information concerning properties including, but not limited to, dishing, erosion, profile, thickness of thin films and critical dimensions of features present on the surface can be extracted. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the chemical properties of the surface, the planarity of the surface, features on the surface, voids in the surface, and the number and/or type of layers beneath the surface. In the present invention, the intensity and/or phase of the reflected and/or diffracted light will be examined as it relates to critical dimensions desired on the wafer being etched.

Different combinations of the above-mentioned properties will have different effects on the phase and/or intensity of the incident light resulting in substantially unique intensity/phase signatures in the complex reflected and/or diffracted light. Thus, by examining a signal (signature or stored value) library of intensity/phase signatures, a determination can be made concerning the properties of the surface. Such substantially unique phase/intensity signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N=n-jk,$$

where j is an imaginary number.

The signature library can be constructed from observed intensity/phase signatures and/or signatures generated by modeling and simulation. By way of illustration, when exposed to a first incident light of known intensity, wavelength and phase, a first feature on a wafer can generate a first phase/intensity signature. Similarly, when exposed to the first incident light of known intensity, wavelength and phase, a second feature on a wafer can generate a second phase/intensity signature. For example, a line of a first width may generate a first signature while a line of a second width may generate a second signature. Observed signatures can be combined with simulated and modeled signatures to form the signature library. Simulation and modeling can be employed to produce signatures against which measured phase/intensity signatures can be matched. In one exemplary aspect of the present invention, simulation, modeling and observed signatures are stored in a signature library containing over three hundred thousand phase/intensity signatures. Thus, when the phase/intensity signals are received from scatterometry detecting components, the phase/intensity signals can be pattern matched, for example, to the library of signals to determine whether the signals correspond to a stored signature.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including any reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A system for monitoring and optimizing an on-going CMP process comprising:

a wafer structure, wherein the wafer structure is subjected to the CMP process;

a CMP device comprising one or more CMP components, wherein the CMP device performs the CMP process;

a CMP process monitoring system for generating a signature related to wafer dimensions for the wafer structure subjected to the CMP process;

a signature library to which the generated signature is compared to determine a state of the wafer structure; and a closed-loop feedback control system coupled to the CMP process monitoring system, the control system comprising a CMP controller such that the control system modifies the on-going CMP process according to the determined state of the wafer structure via the CMP controller.

2. The system of claim 1, further comprising a trained neural network to facilitate optimization of the on-going CMP process.

3. The system of claim 1, wherein the CMP process monitoring system comprises a scatterometry system.

4. The system of claim 1, wherein wafer dimensions comprise a thickness and a profile of the wafer.

5. The system of claim 1, wherein the generated signature corresponds to one of a profile, a thickness, or a combination thereof.

6. An in-line system for monitoring and optimizing an on-going CMP process comprising:
   a CMP device comprising one or more CMP components, wherein the CMP device performs the CMP process;
   a light source for directing light at the wafer, wherein the wafer is subjected to the CMP process;
   a light detector for collecting light reflected from the wafer;
   a signature library comprising signatures associated with known wafers;
   a CMP analysis system operatively coupled to the light detector and the signature library for generating a signature corresponding to the reflected light to determine dimensions of the wafer undergoing the CMP process; and
   a closed-loop feedback control system coupled to the CMP process monitoring system, the control system comprising a CMP controller such that the control system optimizes the on-going CMP process according to the determined wafer dimensions to make one or more changes to the CMP device via the CMP controller.

7. The system of claim 6, further comprising a trained neural network to facilitate optimization of the on-going CMP process.

8. The system of claim 6, wherein the signature library comprises signatures of known wafers as they appear before, during, and after the CMP process.

9. The system of claim 6, wherein the wafer dimensions comprise at least one of a thickness and a profile of the wafer.

10. The system of claim 6, wherein the generated signature corresponds to at least one of a wafer profile, a wafer thickness, or a combination thereof.

11. The system of claim 6, wherein the CMP analysis system comprises a scatterometry system.

12. An in-line system for determining an endpoint of a CMP process using scatterometry comprising:
   a CMP device comprising one or more CMP components, wherein the CMP device performs the CMP process;
   a light source for directing light at a wafer, wherein the wafer is subjected to the CMP process;
   a light detector for collecting light reflected from the wafer;
   a signature library comprising signatures associated with known wafers;
   a CMP monitoring system, operatively coupled to the light detector and the signature library, for generating a signature associated with the reflected light to determine dimensions of the wafer undergoing the CMP process; and
   a CMP controller, operatively coupled to the CMP monitoring system and a CMP driving system, for determining the endpoint of the CMP process, wherein the CMP controller regulates the CMP process by adjusting the one or more CMP components via the CMP driving system using closed-loop feedback control; and
   a trained neural network operatively connected to the CMP controller to facilitate optimization of the CMP process.

13. The system of claim 12, wherein the signature library comprises signatures of known wafers as they appear before, during, and after the CMP process.

14. The system of claim 12, wherein wafer dimensions comprise at least one of a thickness and a profile of the wafer.

15. The system of claim 12, wherein the generated signature corresponds to at least one of a profile, a determined thickness, or a combination state of the wafer structure comprises feeding information relating to the state of the wafer via a closed loop feedback control system to a CMP controller, wherein the CMP controller is connected to a trained neural network to facilitate optimization of the CMP process.

16. An in-line method for monitoring a CMP process comprising:
   providing a wafer structure, wherein the wafer structure Is subjected to a CMP process;
   generating a signature associated with the wafer structure;
   comparing the generated signature to a signature library to determine a state of the wafer structure; and
   using a closed-loop feedback control system, the control system comprising a CMP controller such that the control system modifies the on-going CMP process according to the determined state of the wafer structure via the CMP controller.

17. The method of claim 16, wherein a scatterometry system is employed to generate the signature associated with the wafer structure.

18. The method of claim 17, wherein generating the signature comprises:
   directing a beam of incident light at the wafer structure;
   collecting light reflected from the wafer structure; and
   transforming the reflected light into the signature.

19. The method of claim 16, wherein the signature corresponds to a particular thickness and profile associated with the wafer structure as it appears before, during and after the CMP process.

20. The method of claim 16, wherein an analysis system compares the generated signature to the signature library to determine the state of the wafer structure.

21. The method of claim 16, wherein using a closed-loop feedback control system for modifying the on-going CMP process according to the determined before, during and after the CMP process.

22. An in-line, closed-loop method for determining an endpoint for a CMP process using scatterometry comprising:
   providing a wafer structure, wherein the wafer structure is subjected to a CMP process;
   directing a beam of incident light at the wafer structure;
   collecting light reflected from the wafer structure;
   generating a signature associated with the wafer structure;
   comparing the generated signature to a signature library to determine dimensions of the wafer structure;
   determining whether the wafer structure dimensions are within a pre-determined acceptable range;
   if the wafer structure dimensions are within the acceptable range of values, then instructing a CMP driving system via a CMP controller to terminate the CMP process; and if the wafer structure dimensions are not within the acceptable range of values, then instructing the CMP driving system via a controller to adjust one or more CMP process components and to continue the CMP process for the wafer structure.

23. The method of claim 22, wherein a CMP controller and a trained neural network connected thereto are employed to determine whether the wafer structure dimensions are within a pre-determined acceptable range of values.

24. The method of claim 22, wherein the signature corresponds to a particular thickness and profile associated with the wafer structure as it appears thereof.

25. The method of claim 22, wherein a monitoring system compares the generated signature to the signature library to determine the dimensions of the wafer.

26. A system for monitoring a CMP process comprising:

means for providing a wafer, wherein the wafer is subjected to a CMP process;

means for generating a signature associated with the wafer;

means for comparing the generated signature to a signature library to determine a state of the wafer; and means for using a closed-loop feedback control system, the control system comprising a CMP controller such that the control system modifies the on-going CMP process according to the determined state of the wafer structure via the CMP controller.

* * * * *